United States Patent
Kendrick et al.

(10) Patent No.: US 9,220,573 B2
(45) Date of Patent: Dec. 29, 2015

(54) SYSTEM AND METHOD FOR TRACKING POSITIONS OF UNIFORM MARKER GEOMETRIES

(75) Inventors: Lance Kendrick, Lafayette, CO (US); Andrew Bzostek, Erie, CO (US); Vince J. Doerr, Boulder, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1244 days.

(21) Appl. No.: 11/649,321

(22) Filed: Jan. 2, 2007

(65) Prior Publication Data
US 2008/0161682 A1   Jul. 3, 2008

(51) Int. Cl.
*A61B 19/00* (2006.01)
*A61B 17/00* (2006.01)

(52) U.S. Cl.
CPC ............ *A61B 19/5244* (2013.01); *A61B 19/52* (2013.01); *A61B 19/54* (2013.01); *A61B 19/50* (2013.01); *A61B 2017/00221* (2013.01); *A61B 2019/505* (2013.01); *A61B 2019/5238* (2013.01); *A61B 2019/5251* (2013.01); *A61B 2019/5255* (2013.01); *A61B 2019/5265* (2013.01); *A61B 2019/5291* (2013.01); *A61B 2019/5445* (2013.01); *A61B 2019/5479* (2013.01); *A61B 2019/5483* (2013.01); *A61B 2019/566* (2013.01)

(58) Field of Classification Search
USPC .......... 382/131; 600/407, 410, 424, 426, 473, 600/476; 702/150
See application file for complete search history.

(56) References Cited

U.S. PATENT DOCUMENTS

| | | | | |
|---|---|---|---|---|
| 5,834,759 | A * | 11/1998 | Glossop | 250/203.1 |
| 6,026,315 | A | 2/2000 | Lenz et al. | |
| 6,131,296 | A * | 10/2000 | Fager | 33/293 |
| 2002/0193685 | A1* | 12/2002 | Mate et al. | 600/424 |
| 2004/0138556 | A1* | 7/2004 | Cosman | 600/424 |
| 2005/0020909 | A1 | 1/2005 | Moctezuma de la Barrera et al. | |
| 2005/0201613 | A1* | 9/2005 | Mostafavi | 382/154 |
| 2005/0245817 | A1* | 11/2005 | Clayton et al. | 600/424 |
| 2006/0241399 | A1* | 10/2006 | Fabian | 600/424 |
| 2006/0264742 | A1* | 11/2006 | Neubauer et al. | 600/424 |
| 2007/0016009 | A1* | 1/2007 | Lakin et al. | 600/424 |

FOREIGN PATENT DOCUMENTS

DE   19813383   10/1999
EP   1415609   5/2004

OTHER PUBLICATIONS

International Search Report and Written Opinion for PCT/US2007/026308 mailed May 9, 2008.

* cited by examiner

*Primary Examiner* — Rochelle Turchen
(74) *Attorney, Agent, or Firm* — Harness, Dickey (57) ABSTRACT

A system and method for tracking a tracking device for use with a surgical navigation system is provided. The system and method can include at least one tracking device having a plurality of faces. The faces can be operable to generate a signal upon activation. Also included is a face activation module that activates a selected one of the faces upon receipt of an activation signal. The system can also include a visibility module that generates the activation signal and receives the signal from the face to generate tracking data for the tracking device, along with a face switching module that generates a face control signal to activate a different face based on the tracking data.

35 Claims, 5 Drawing Sheets

SYSTEM AND METHOD FOR TRACKING POSITIONS OF UNIFORM MARKER GEOMETRIES

FIELD

The present disclosure relates generally to navigated surgery, and more specifically, to systems and methods for tracking positions of uniform marker geometries.

BACKGROUND

The statements in this section merely provide background information related to the present disclosure and may not constitute prior art.

Image guided medical and surgical procedures utilize patient images obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), fluoroscopic imaging (such as with a C-arm device), positron emission tomography (PET), and ultrasound imaging (US) has increased the interest in image guided medical procedures.

Typical image guided navigation systems require dynamic reference frames to track the position of the patient should patient movement occur during the assisted procedure. The dynamic reference frame (DRF) is generally affixed to the patient in a generally permanent or immovable fashion. The DRF can include a tracking device that has multiple markers that are trackable by the navigation or tracking system. In addition, many navigation systems generally employ a tracking device having multiple markers coupled to an instrument or the imaging device to enable the instrument or imaging device to be tracked.

In order to properly track the navigated instrument, imaging device and, optionally, track the position of the patient through the DRF, the instrument, the imaging device and the DRF must be distinguishable at all orientations by the navigation or tracking system. Generally, in order to ensure the instrument, the imaging device and the DRF are viewable at all orientations for an optical tracking system, the instrument, the imaging device and the DRF can each include a tracking device that employs multiple markers. Each marker can typically include a light emitting or light reflecting object. The tracking device also includes multiple faces, with each face distinguishable at all orientations. For each face of the tracking device, the light emitting or light reflecting objects can be arranged in a unique pattern such that each face of the tracking device has an easily identifiable signature pattern of light emitting or light reflecting objects.

Typically, to form the unique pattern of the light emitting or light reflecting objects, each light emitting or light reflecting object on the particular face is spaced a unique distance away from each of the other light emitting or light reflecting objects on that face. Thus, as the number of faces on the tracking device increases, in order to form the unique pattern of light emitting or light reflecting objects, the light emitting or light reflecting objects must be spaced further and further apart. This increased spacing of the light emitting or light reflecting objects on the faces to form a unique pattern for each face causes the size of the faces on the tracking device to increase, which can be undesirable when using multiple faced tracking device to navigate size or weight-constrained devices. Accordingly, it can be desirable to provide a system and method for tracking positions of tracking devices that utilize uniform marker geometries, such as light emitting or light reflecting objects.

SUMMARY

A system for tracking a tracking device for use with a surgical navigation system. The system can include at least one tracking device having a plurality of faces. The faces can be operable to generate a signal upon activation. The system can also include a face activation module that activates a selected one of the faces upon receipt of an activation signal. The system can include a visibility module that generates the activation signal and receives the signal from the face to generate tracking data for the tracking device and a face switching module that generates face control data to activate a different face based on the tracking data.

Provided is a method of tracking a tracking device for use with a surgical navigation system. The method can include providing at least one tracking device having a plurality of faces and activating a selected one of the faces to emit a signal. The method can also include tracking the signal emitted by the selected face and determining, based on the tracking of the selected face, if a different one of the faces should be activated.

A method of tracking a portion of an anatomy is further provided. The method can include coupling a tracking device having a plurality of faces to at least one of the anatomy or an instrument. The method can also include tracking the tracking device relative to within the anatomy by: activating the tracking device to illuminate a selected face, tracking the illumination of the selected face and determining, based on the illumination of the selected face, if a different one of the plurality of faces should be illuminated.

Further provided is a surgical navigation system. The surgical navigation system can comprise at least one tracking device having a plurality of faces that are illuminated in an active state. The system can also include a tracking system that tracks the tracking device and determines which one of the faces to activate. The surgical navigation system can also include a display device that displays a position of the tracking device during the surgical procedure.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features. As indicated above, the present teachings are directed towards providing an improved system and method for the tracking of a tracking device including a plurality of markers without requiring the use of unique geometries to identify marker positions in a navigated surgical procedure. It should be noted, however, that the present teachings could be applicable to any appropriate procedure in which the tracking of a tracking device is required. Further, as used herein, the term module refers to an application specific integrated circuit (ASIC), an electronic circuit, a processor (shared, dedicated, or group) and memory that executes one or more software or firmware programs, a combinational logic circuit, separate software or firmware modules and/or other suitable components that provide the described functionality. Therefore, it will be understood that the following discussions are not intended to limit the scope of the appended claims.

Figure 1:
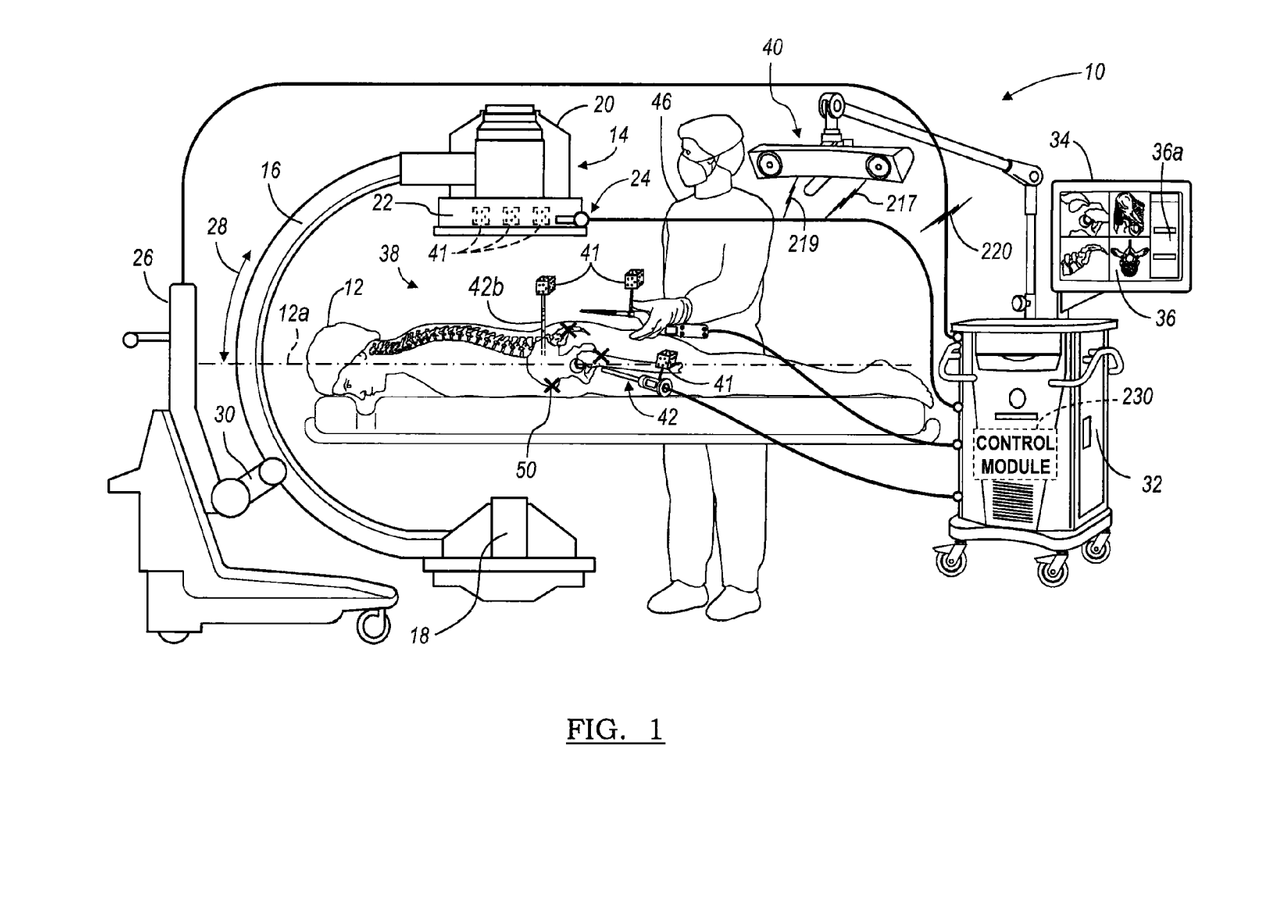
FIG. 1 is a diagram of a navigation system according to various embodiments of the present disclosure.

FIG. 1 is a diagram illustrating an overview of a navigation system 10 that can be used for various procedures. The navigation system 10 can be used to track the location of an implant, such as a spinal implant or orthopedic implant, relative to a patient 12 Also the navigation system 10 can track the position and orientation of various instruments. It should further be noted that the navigation system 10 may be used to navigate any type of instrument, implant, or delivery system, including: guide wires, arthroscopic systems, orthopedic implants, spinal implants, deep-brain stimulator (DBS) probes, a catheter, a reference frame, microscopes, drills and drill-guides, suctions, biopsy needles, cutting guides, etc. Moreover, these instruments may be used to navigate or map any region of the body. The navigation system 10 and the various instruments may be used in any appropriate procedure, such as one that is generally minimally invasive or an open procedure.

The navigation system 10 may include an imaging device 14 that is used to acquire pre-, intra-, or post-operative or real-time image data of the patient 12. Alternatively various imageless systems can be used or images from atlas models can be used to produce patient images, such as those disclosed in U.S. Patent Pub. No. 2005-0085714, filed Oct. 16, 2003, entitled "METHOD AND APPARATUS FOR SURGICAL NAVIGATION OF A MULTIPLE PIECE CONSTRUCT FOR IMPLANTATION", incorporated herein by reference. The imaging device 14 is, for example, a fluoroscopic x-ray imaging device that may be configured as an O-arm™ or a C-arm 16 having an x-ray source 18, an x-ray receiving section 20, an optional calibration and tracking target 22 and optional radiation sensors 24.

Image data may also be acquired using other imaging devices, such as those discussed above and herein. An imaging device controller 26, that may control the C-arm 16, can capture the x-ray images received at the receiving section 20 and store the images for later use. The controller 26 may also be separate from the C-arm 16 and/or control the rotation of the C-arm 16. For example, the C-arm 16 can move in the direction of arrow 28 or rotate about a longitudinal axis 12a of the patient 12, allowing anterior or lateral views of the patient 12 to be imaged. Each of these movements involves rotation about a mechanical axis 30 of the C-arm 16.

In the example of FIG. 1, the longitudinal axis 12a of the patient 12 is substantially in line with the mechanical axis 30 of the C-arm 16. This enables the C-arm 16 to be rotated relative to the patient 12, allowing images of the patient 12 to be taken from multiple directions or about multiple planes. An example of a fluoroscopic C-arm x-ray device that may be used as the imaging device 14 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc. An exemplary O-arm™ imaging device is available from Breakaway Imaging, LLC of Littleton, Mass.

In operation, the imaging device 14 generates x-rays from the x-ray source 18 that propagate through the patient 12 and calibration and/or tracking target 22, into the x-ray receiving section 20. It will be understood that the tracking target 22 need not include a calibration portion. The receiving section 20 generates image data representing the intensities of the received x-rays. Typically, the receiving section 20 includes an image intensifier that first converts the x-rays to visible light and a charge coupled device (CCD) video camera that converts the visible light into digital image data. Receiving section 20 may also be a digital device that converts x-rays directly to digital image data for forming images, thus potentially avoiding distortion introduced by first converting to visible light. Alternatively, the imaging device 14 may only take a single image with the calibration and tracking target 22 in place. Thereafter, the calibration and tracking target 22 may be removed from the line-of-sight of the imaging device 14. The tracking target 22 can enable the navigation system 10 to track the location of the imaging device 12 via at least one tracking device coupled to the tracking target 22, as will be discussed herein. When the x-ray source 18 generates the x-rays that propagate to the x-ray receiving section 20, the radiation sensors 24 sense the presence of radiation, which is forwarded to the controller 26, to identify whether or not the imaging device 14 is actively imaging.

Two dimensional fluoroscopic images that may be taken by the imaging device 14 are captured and stored in the controller 26. Multiple two-dimensional images taken by the imaging device 14 may also be captured and assembled to provide a larger view or image of a whole region of a patient, as opposed to being directed to only a portion of a region of the patient 12. For example, multiple image data of a patient's leg may be appended together to provide a full view or complete set of image data of the leg that can be later used to follow contrast agent, such as Bolus tracking.

The image data is then forwarded from the controller 26 to a navigation computer and/or processor, controller or workstation 32 having a display 34 and a user interface 36. It will also be understood that the image data is not necessarily first retained in the controller 26, but may also be directly transmitted to the workstation 32. The workstation 32 provides facilities for displaying the image data as an image on the display 34, saving, digitally manipulating, or printing a hard copy image of the of the received image data. The user interface 36 can comprise any device, such as an user input device 36a, that can enable a user to interface with the workstation 32, such as a touchpad, touch pen, touch screen, keyboard, mouse, wireless mouse, or a combination thereof. The user interface 36 allows a physician or user to control the navigated surgical procedure.

While the imaging device 14 is shown in FIG. 1, any other alternative 2D, 3D or 4D imaging modality may also be used. For example, any 2D, 3D or 4D imaging device, such as an O-arm imaging device, isocentric fluoroscopy, bi-plane fluoroscopy, ultrasound, computed tomography (CT), multi-slice computed tomography (MSCT), magnetic resonance imaging (MRI), high frequency ultrasound (HFU), positron emission tomography (PET), optical coherence tomography (OCT), intra-vascular ultrasound (IVUS), ultrasound, intra-operative CT or MRI may also be used to acquire 2D, 3D or 4D pre- or post-operative and/or real-time images or image data of the patient 12. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, could also provide functional image data superimposed onto anatomical data to be used to confidently reach target sites within the patient 12. It should further be noted that the imaging device 14, as shown in FIG. 1, provides a virtual bi-plane image using a single-head C-arm fluoroscope as the imaging device 14 by simply rotating the C-arm 16 about at least two planes, which could be orthogonal planes to generate two-dimensional images that can be converted to three-dimensional volumetric images. By acquiring images in more than one plane, an icon representing the location of an impacter, stylet, reamer driver, taps, drill, or other instrument, introduced and advanced in the patient 12, may be superimposed in more than one view on display 34 allowing simulated bi-plane or even multi-plane views, including two and three-dimensional views, as will be discussed in greater detail herein.

With continuing reference to FIG. 1, if the navigation system 10 is a line-of-sight system, the navigation system 10 can further include an optical tracking system 38. The tracking system 38 can include a camera 40 and tracking devices 41 attached to various instruments, implants 42 and/or the imaging device 14. The camera 40 can be an optical localizer such as used in the StealthStation® TRIA™ sold by Medtronic Navigation of Louisville, Colo. The instruments 42 can include an instrument 42a for use in the procedure and a dynamic reference frame or DRF 42b. Each of the instruments 42 can include either passive or active reflective tracking devices 41 that can be attached to the instruments 42, and can include markers 200 as will be discussed in greater detail herein. In addition, the tracking target 22 of the imaging device 14 can be comprised of at least one tracking device 41 to enable the navigation system 10 to determine the location of the imaging system 44. The optical tracking system 38 is generally considered a line-of-sight tracking system as the instruments 42 are tracked based on their optical visibility to the camera 40.

The instrument 42a may be any appropriate instrument, such as an instrument for preparing a portion of the patient or positioning an implant. The instrument 42a can also be a handle or inserter that interconnects with an attachment and may assist in placing an implant or in driving a portion. The instrument 42a can include a graspable or manipulable portion at a proximal end and the tracking device 41 may be fixed near the manipulable portion of the instrument 42a, as will be discussed in greater detail herein. The DRF 42b may be fixed to the patient 12 adjacent to the region being navigated so that any movement of the patient 12 is detected. The DRF 42b may include any appropriate tracking device, such as tracking device 41, recognized by the navigation system 10.

Briefly, the navigation system 10 operates as follows. The navigation system 10 creates a translation map between all points in the radiological image generated from the imaging device 14 and the corresponding points in the patient's anatomy in patient space. After this map is established, whenever a tracked instrument, such as the instrument 42a or a pointing device or probe 44 is used, the workstation 32 in combination with the tracking system 38 and the controller 26 uses the translation map to identify the corresponding point on the pre-acquired image or atlas model, which is displayed on display 34. This identification is known as navigation or localization. An icon representing the localized point or instruments is shown on the user interface 36 within several two-dimensional image planes, as well as on three and four dimensional images and models, as will be discussed herein.

To enable navigation, the navigation system 10 must be able to detect both the position of the patient's anatomy and the position of the instrument 42a or attachment member attached to the instrument 42a. Knowing the location of these two items allows the navigation system 10 to compute and display the position of the instrument 42a in relation to the patient 12. The tracking system 38 is employed to track the instrument 42a and the anatomy simultaneously.

The tracking system 38 essentially works by using the camera 40 adjacent to the patient space to generate a visual field, referred to as a navigation field. The DRF 42b is fixed to the patient 12 to identify the location of the patient 12 in the navigation field. The tracking system 38 continuously recomputes the relative position of the DRF 42b and the instrument 42a during localization and relates this spatial information to patient registration data to enable image guidance of the instrument 42a within and/or relative to the patient 12.

Patient registration is the process of determining how to correlate the position of the instrument 42a relative to the patient 12 to the position on the diagnostic or pre-acquired images. To register the patient 12, a physician or user 46 may use point registration by selecting and storing particular points from the pre-acquired images and then touching the corresponding points on the patient's anatomy with the pointer probe 44. The navigation system 10 analyzes the relationship between the two sets of points that are selected and computes a match, which correlates every point in the image data or image space with its corresponding point on the patient's anatomy or the patient space, as discussed herein. The points that are selected to perform registration are the fiducial markers or markers 50, such as anatomical landmarks. Again, the landmarks or fiducial markers 50 are identifiable on the images and identifiable and accessible on the patient 12. The fidicial markers 50 can be artificial markers 50 that are positioned on the patient 12 or anatomical landmarks that can be easily identified in the image data. The artificial landmarks, such as the fiducial markers 50, can also form part of the DRF 42b, such as those disclosed in U.S. Pat. No. 6,381,485, entitled "Registration of Human Anatomy Integrated for Electromagnetic Localization," issued Apr. 30, 2002, herein incorporated by reference.

The navigation system 10 may also perform registration using anatomic surface information or path information as is known in the art. The navigation system 10 may also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 60/465,615, entitled "Method and Apparatus for Performing 2D to 3D Registration" filed on Apr. 25, 2003, hereby incorporated by reference.

The navigation system 10 can be used according to any appropriate method or system. For example, pre-acquired images, atlas or 3D models may be registered relative to the patient and patient space. Generally, the navigation system 10 allows the images on the user interface 36 to be registered and to accurately display the real time location of the various instruments, such as the instrument 42*a*, and other appropriate items, such as the pointer probe 44. In addition, the pointer probe 44 may be used to register the patient space to the pre-acquired images or the atlas or 3D models. In addition, the DRF 42*b* may be used to ensure that any planned or unplanned movement of the patient is determined and used to correct the image on the display 34.

It will be understood that the tracking system employed with the navigation system 10 may also be a hybrid tracking system, and can include both optical and electromagnetic (EM) tracking system components. Further detail regarding the EM tracking system is outside the scope of the present disclosure but is disclosed in greater detail in U.S. patent application Ser. No. 10/941,782, filed Sep. 15, 2004, and entitled "METHOD AND APPARATUS FOR SURGICAL NAVIGATION", herein incorporated by reference. Further, other tracking systems could be employed with the tracking system 38 for use by the navigation system 10, such as an acoustic, radiation, etc.

If the tracking system 38 employed is the optical tracking system 38, the instrument 42*a*, DRF 42*b* and tracking target 22 can include at least one active or passive optical tracking device 41 including a plurality of optical or passive markers 200. If an active tracking device 41 is employed, the active tracking device 41 can include active optical markers 200. Each of the active optical markers 200 can include a light emitting feature, such as an infrared light emitting diode, that can be recognized by the camera 40. Alternatively, a passive optical marker 200 could include at least one reflector to reflect an optical beam generated by the camera 40.

Figure 2:
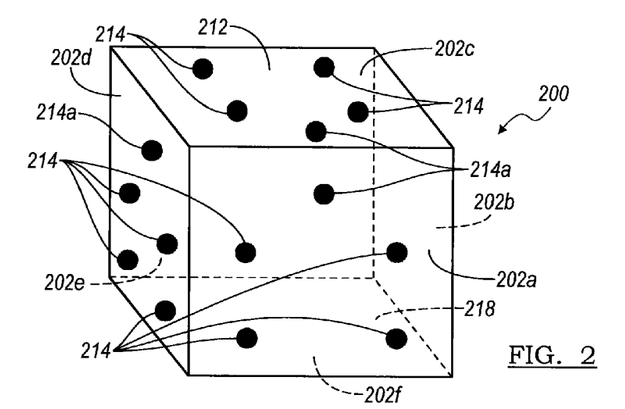
FIG. 2 is a detailed perspective view of an exemplary geometrically uniform tracking device including a plurality of markers of FIG. 1.

With continuing reference to FIG. 1 and with additional reference to FIG. 2, an exemplary tracking device 41 including an active marker 200 is shown. The tracking device 41 enables the instrument 42*a* and, optionally, the DRF 42*b* to be located by the camera 40. In this regard, the markers 200 on the tracking device 41 can generate a signal, such as a reflection or an emission of infrared (IR) light, which is visible or recognizable by the camera 40. The camera 40 can then transmit this image or signal to the workstation 32. The workstation 32 can then locate the instrument 42*a*, the DRF 42*b* and/or imaging device 14 relative to the patient 12 based on the signal received by the camera 40 from the markers 200. The tracking device 41 can employ at least three markers 200 to enable the determination of the position of the instrument 42 and/or imaging device 14, but generally include at least six markers 200 so that both the position and the orientation of the instrument 42 and/or imaging device 14 can be determined.

In various embodiments, with reference to FIG. 2, the tracking device 41 can include a first face 202*a*, a second face 202*b*, a third face 202*c*, a fourth face 202*d*, a fifth face 202*e* and a sixth face 202*f*. For simplicity, the tracking device 41 is illustrated as cubic with six defined faces 202, however, it will be understood that the tracking device 41 can include any number of faces, and can be in any appropriate shape, such as spherical, hexagonal or the like. In addition, it will be understood herein that the reference numeral 202, as used herein, can refer to any of the faces 202*a*, 202*b*, 202*c*, 202*d*, 202*e*, 202*f*. The number of faces 202 on the tracking device 41 can be proportional to the desired accuracy of the application. Typically, by providing a tracking device 41 with a larger number of faces 202, any slight movement of the tracking device 41 can be tracked due to the availability of a new face 202 to be observed by the camera 40. Thus, the greater the number of faces 202 of the tracking device 41, the greater the accuracy of the visibility of the markers 200 on the tracking device 41 with respect to the patient 12.

The tracking device 41 can be coupled to a desired device, such as the instrument 42, through any appropriate technique, such as through the use of adhesives and/or mechanical fasteners, and can include attachment features, such as a stem (not shown) to facilitate such coupling or could be formed in the handle of the instrument 42 as shown. The tracking device 41 can also include at least one or a plurality of markers 200 or light emitting diodes (LEDs), a receiver 216 and a controller 218. It should be noted that although the tracking device 41 is illustrated and described herein as employing IR light emitting markers 200, the tracking device 41 could employ a passive tracking system, through the use of selectively active reflectors, for example. In addition, it should be noted that although the tracking device 41 is illustrated as having a solid surface embedded with markers 200, the markers 200 could be coupled to the tracking device 41 or instrument 42 such that the markers 200 themselves form the faces 202.

Figure 3:
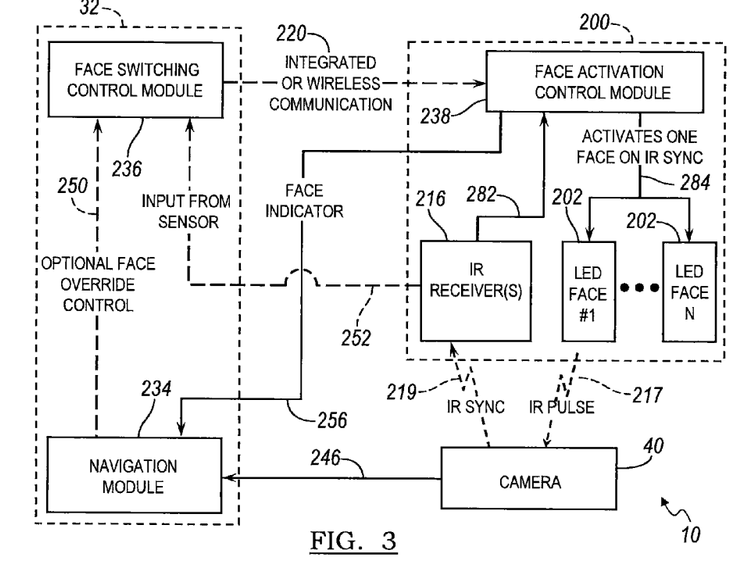
FIG. 3 is a simplified block diagram illustrating an exemplary navigation system for use with a marker control module.

With continuing reference to FIG. 3, the markers 200 can be activated to emit a signal, such as an IR light pulse 217, for example. The emission of the IR pulse 217 can be sensed by the camera 40 and used to determine the three-dimensional position of the tracking device 41 with respect to the patient 12, as discussed herein. Generally, the markers 200 are charged to emit the IR pulse 217 by an external source, such as a suitable IR sync 219 received from the camera 40. The IR sync 219 can comprise an emission of IR light that charges the markers 200.

With reference to FIG. 2, the markers 200 on each of the faces 202 of the tracking device 41 can be arranged in an identical or uniform geometric pattern. As the faces 202 have a similar geometric pattern, even if a large number of faces 202 are employed with the tracking device 41 the similar geometric pattern enables the size of the tracking device 41 to meet the anatomic, mechanical and ergonomic requirements for the item to which it is attached, such as instrument 42. In the geometric pattern, each of the faces 202 can include one marker 200*a* that is extended a greater distance from the other markers 200 on each of the faces 202 to enable the camera 40 to identify, via the IR pulse 217 obtained from the marker 200*a*, the orientation, such as up or down, of the tracking device 41. For example, the marker 200*a* can be spaced a particular distance from the remainder of the markers 200 on the face 202 such that based on the difference between the spacing of the markers 200 on the face 202, the orientation of that particular face 202 can be identified with respect to the camera 40. It should be noted that although each of the faces 202 are shown to include five markers 200, any appropriate number of markers 200 could be employed, such as three, depending upon the desired accuracy and redundancy required for the tracking device 41.

With reference to FIGS. 2 and 3, the receiver 216 can be coupled to the markers 200 such that the receiver 216 can receive the IR sync 219 from the camera 40. The receiver 216 is in communication with the controller 218 to transmit a signal indicative of the receipt of the IR sync 219 to the controller 218. The controller 218 can receive the signal regarding the IR sync 219, and a wireless face data signal 220 from the workstation 32, as will be discussed herein. The wireless face data signal 220 can comprise a signal from the workstation 32 to activate a selected face 202 of the marker 200. By activating a known face 202, each face 202 can be geometrically identical with regard to the position of the markers 200 on each face 202 as the workstation 32 knows which of the faces 202 is being viewed by the camera 40. In other words, as the workstation 32 knows which of the faces 202 is active, the face 202 viewed by the camera 40 can be localized without requiring each of the faces 202 to have a specific, individually identifiable geometric pattern of markers 200.

With continuing reference to FIG. 3, based on the receipt of the IR sync 219 and the wireless face data signal 220, the controller 218 can activate the selected face 202 of the tracking device 41, as will be discussed herein. Generally, the tracking device 41 can be in wireless communication with the workstation 32, however, the tracking device 41 could be in wired communication with the workstation 32, if desired. If the tracking device 41 is in wireless communication with the workstation 32, then both of the tracking device 41 and workstation 32 can include suitable transmitters and receivers to enable wireless communication over a suitable wireless protocol, such as Bluetooth, for example. Additional appropriate wireless protocols can include ZigBee™ Alliance, and Wi-Fi® such as IrDA®, Broadband Wireless USB, or IEEE 802.11. An exemplary wireless communication system is discussed in U.S. Pat. No. 6,499,488, entitled "Surgical Sensor" filed on Oct. 28, 1999, hereby incorporated by reference. Generally, the activation of the face 202 of the tracking device 41 can be controlled by a control module 230, as shown in FIG. 3.

With continuing reference to FIG. 3 and with additional reference to FIG. 1, a block diagram schematically illustrates an exemplary navigation system 10 for implementing the control module 230 according to various embodiments. The navigation system 10 can include a navigation module 234, a face switching control module 236, the camera 40 and the tracking device 41 that includes a face activation control module 238, the receiver 216, and the faces 202 including the markers 200. The navigation module 234 can provide tracking data 250 regarding the location of the visible faces 202, the location of the remaining faces 202, and data regarding if any of the remaining faces 202 might or might not be visible to the camera 40 to the face switching control module 236. The navigation module 234 and face switching control module 236 can be implemented on the workstation 32, however, separate computers or workstations could be employed.

Based on the data received from the navigation module 234, the face switching control module 236 can generate face control data 256 that can instruct the face activation control module 238 as to which of the faces 202 on the tracking device 41 to activate. The face switching control module 236 can transmit the wireless face data signal 220 and face control data 256 to the face activation control module 238 over the wireless protocol. The face control data 256 can also be transmitted to the navigation module 234 so that the navigation module 234 is aware of the active face $202|_{[k1]}$, however, it should be noted that the navigation module 234 does not necessarily need to know which face 202 is active so long as only one face 202 is active. Upon receipt of the face control data 256, the face activation control module 238 can generate a signal or activation data 310 to activate the particular face 202 of the tracking device 41 upon receipt of the IR sync 219. The receiver 216 of the tracking device 41 can receive the IR sync 219 and generate IR data 308 that indicates that the IR sync 219 has been received from the camera 40. The controller 218 of the tracking device 41 can receive both the face control data 256 and IR data 308 and then activate the face 202. The activation of the particular face 202 activates the markers 200 on that face 202 such that the markers 200 can generate the IR pulse 217 for the camera 40.

The camera 40 can generate the IR sync 219 and can receive the IR pulse 217. Based on the IR pulse 217 received, the camera 40 can determine localization data 246 for the activated face 202, such as the position and the orientation of the face 202, along with the number of markers 200 visible on that face 202. The camera 40 can also generate the line-of-sight angle for each of the markers 200 viewed by the camera 40. Generally, the line-of-sight angle is the angle between a vector normal to the face 202 of the marker 200 and a line-of-sight of the camera 40. The camera 40 can then transmit this localization data 246 to the navigation module 234, so the navigation module 234 can generate the tracking data 250.

Figure 4:
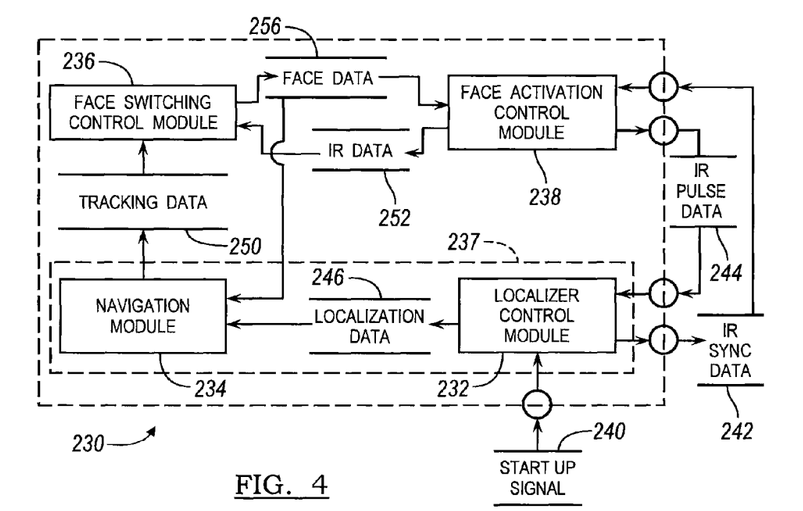
FIG. 4 is a dataflow diagram illustrating an exemplary marker control system performed by the marker control module.

With reference to FIG. 4, a dataflow diagram illustrates various components of a marker control system that can be embedded within the control module 230. Various embodiments of the marker control system according to the present disclosure can include any number of sub-modules embedded within the control module 230. The sub-modules shown may be combined and/or further partitioned to similarly determine which face 202 on the tracking device 41 to activate. Inputs to the system can be received from the C-arm 16, or even received from other control modules (not shown) within the navigation system 10, and/or determined by other sub-modules (not shown) within the control module 230 (not shown). In various embodiments, the control module 230 includes the camera 40 or a localizer control module 232, the navigation module 234, the face switching control module 236, and the face activation control module 238. The localizer control module 232 and the navigation module 234 can form a visibility module 237.

The localizer control module 232 can receive as input a start-up signal 240. The start-up signal 240 can indicate an initialization of the navigation system 10. The localizer control module 232 can output, based on the start-up signal 240, an IR sync data 242 for the face activation control module 238. The IR sync data 242 can comprise the IR sync 219 that is sent from the camera 40 to the tracking device 41. The localizer control module 232 can also receive as input IR pulse data 244 from the face activation control module 238. The IR pulse data 244 can comprise the IR pulse 217 that is generated upon the illumination or activation of a selected face 202 of the tracking device 41. Based on the receipt of the IR pulse data 244, the localizer control module 232 can set localization data 246 for the navigation module 234. The localization data 246 can comprise data regarding the position and the orientation of the face 202, along with the number of markers 200 visible on that face 202 and the line-of-sight associated with the face 202 of the tracking device 41.

The navigation module 234 can receive as input the localization data 246 and face control data 256. The navigation module 234 can determine, based on the localization data 246 and the face control data 256, the location of the visible faces 202, the location of the remaining faces 202, and data regarding if any of the remaining faces 202 might or might not be visible to the camera 40. The navigation module 234 can determine the location of all the other faces 202 as the navigation module 234 can be programmed to know the shape of the tracking device 41, and thus, based on the face control data 256 that indicates which face 202 is active, and the localization data 246, the navigation module 234 can determine the location of the other faces 202. The navigation module 234 can then set tracking data 250 for the face switching control module 236. In addition, the tracking data 250 can optionally include a face activation override control signal that instructs the face switching control module 236 to activate markers 200 on a specific face 202. Using the override signal, the navigation module 234 can take control of the face activation decision, allowing the navigation module 234 to determine which face 202 to activate based on additional or alternative information or control logic, such as user input from the user input device 36a or surgical task-flow information.

The tracking data 250 can be received as input by the face switching control module 236. The face switching control module 236 can also receive as input IR data 252 from the face activation control module 238. The IR data 252 can indicate the receipt of the IR sync 219 by the face activation control module 238. The face switching control module 236 can determine which face 202 of the tracking device 41 to activate based on the tracking data 250 and IR data 252, and sets face control data 256 for the face activation control module 238. The face control data 256 can comprise the desired face 202 to activate.

Figure 5A:
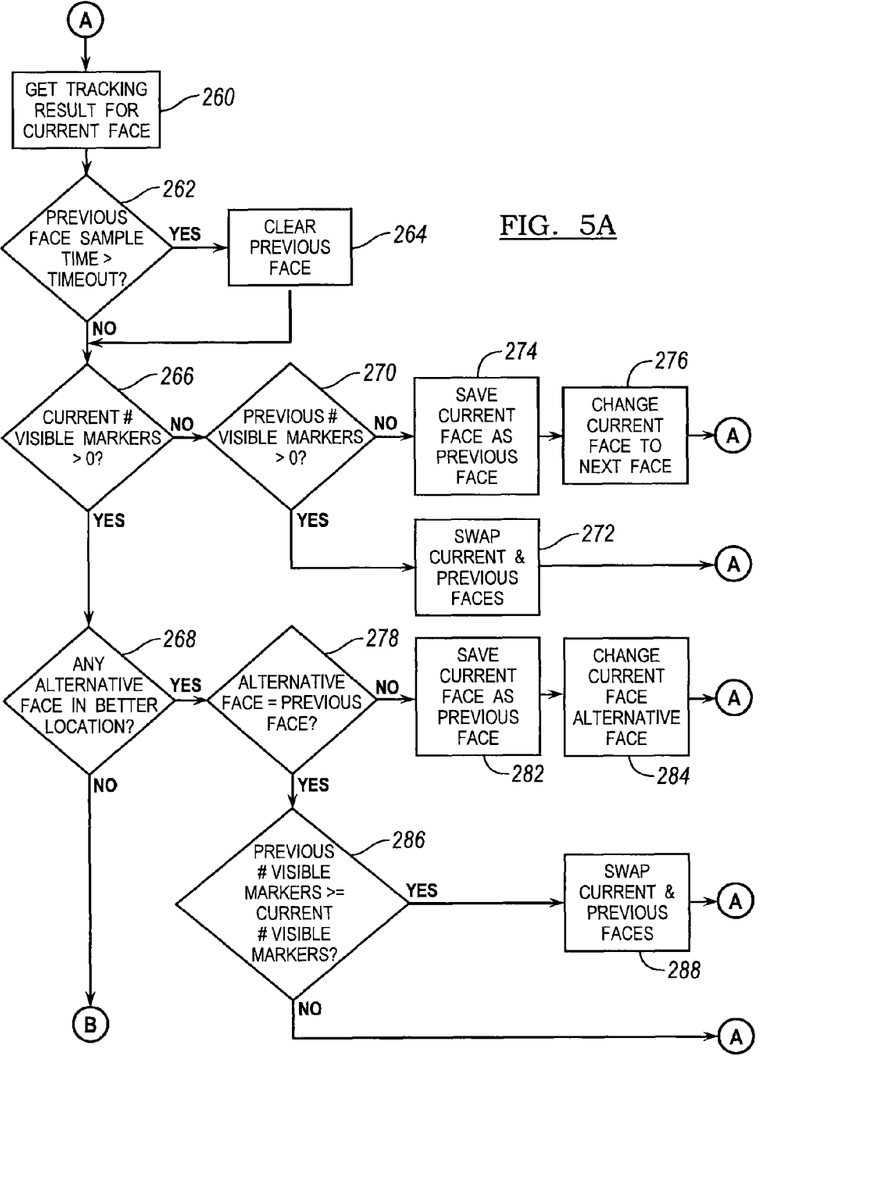
FIG. 5A is a flowchart illustrating a face switching method performed by the face switching control module of the marker control module.

For example, with reference to FIG. 5, a flowchart illustrates a face switching method performed by the face switching control module 236. Upon receipt of the IR data 252, the face switching control module 236 can set face control data 256 comprising the control signal to activate a face 202 of the tracking device 41. Then, at 260, the face switching control module 236 can acquire the tracking data 250 for the current activated face 202 of the tracking device 41. At decision block 262, the method can determine if the previous activated face 202 sample time is greater than a timeout threshold. If the previous activated face 202 sample time is greater than the timeout threshold, then the method clears the previous activated face data at 264. The threshold can be set to any period of time, but is generally long enough so that upon a start-up of the navigation system 10, the previous face data is cleared.

If the previous face 202 sample time is less than the timeout threshold or the data regarding the previous face 202 has been cleared, then the method goes to 266. At decision block 266, the method can determine if the current number of markers 200 visible on the current face 202 is greater than zero. If the current number of visible markers 200 is greater than zero, then control goes to 268. Otherwise, at decision block 270, the method determines if the number of markers 200 that were visible on the previous active face 202 is greater than zero. If the number of visible markers 200 on the previous active face 202 is greater than zero, then the method at 272 switches the current active face 202 with the previously active face 202 and loops to 260. Otherwise, if the number of visible markers 200 on the previous active face 202 is not greater than zero, then the method saves the current face 202 as the previous face 202 at 274. Then, at 276, the method changes the current face 202 to a new face 202. The method then loops to 260.

If the current number of visible markers 200 is greater than zero, the method, at 268, determines, based on the tracking data 250, if any alternative face 202 is in a better location with regard to being better viewed by the camera 40. An alternative face 202 is considered to be in a better position than any other face 202 if the line-of-sight angle for the markers 200 on the alternative face 202 is smaller than the line-of-sight angle associated with the markers 200 on the current face 202. Typically, the line-of-sight angle associated with markers 200 can range from positive 50 degrees to negative 50 degrees with respect to the normal vector. If another face 202 has a line-of-sight angle that is less than or smaller than the line-of-sight angle of the current face 202, then the method goes to decision block 278. If another face 202 does not have a line-of-sight angle that is less than the line-of-sight angle of the current face 202, then the method goes to decision block 280.

At decision block 278, the method can determine if the alternative face 202 is the previous face 202. If the alternative face 202 is not the previous face 202, then at 282, the method saves the current face 202 as the previous face 202. Next, at 284, the method can change the current face 202 to the alternative face 202. Then, the method loops to 260.

If the alternative face 202 is the previous face 202, then the method goes to decision block 286. At decision block 286, the method can determine if the previous number of visible markers 200 was greater than or equal to the current number of visible markers 200. If the previous number of visible markers 200 is greater than or equal to the current number of visible markers 200, then the method goes to 288. At 288, the method can swap the current face 202 with the previous face 202. The method then loops to 260. If the previous number of visible markers 200 is not greater than or equal to the current number of visible markers 200, then the method loops to 260.

Figure 5B:
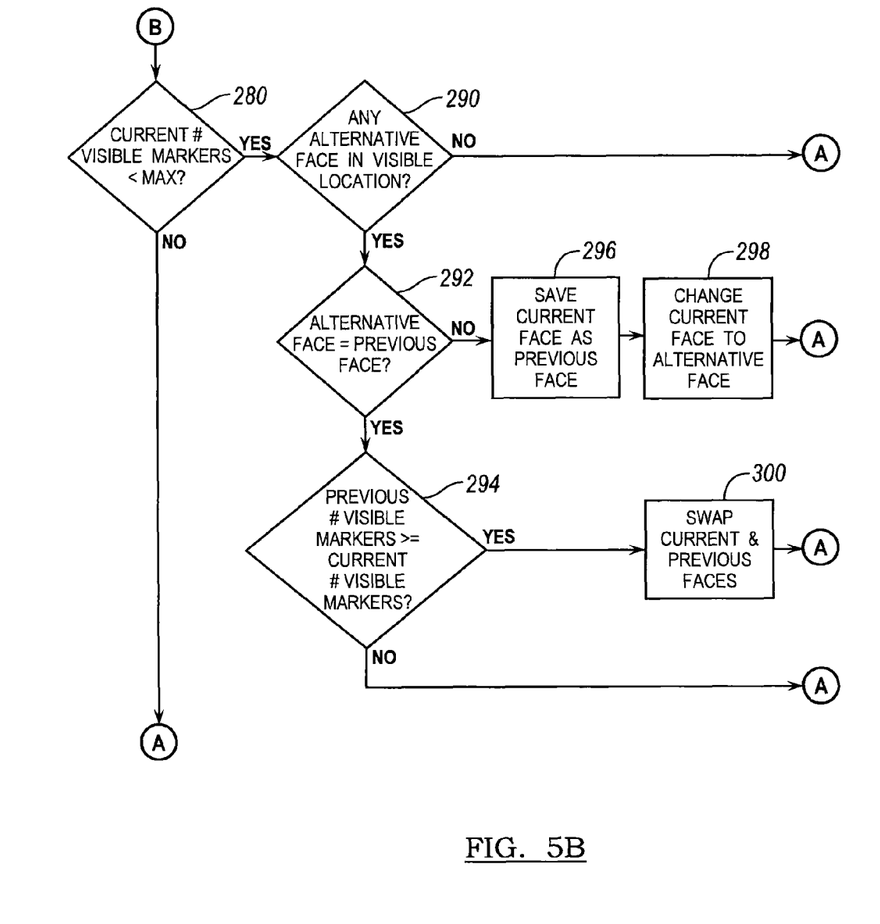
FIG. 5B is a continuation of the flowchart of FIG. 5A at B.

At decision block 280, the method can determine if the current number of visible markers 200 is less than a maximum number of markers 200 that could be visible on the face 202. Thus, for example, as there are five markers 200 on each face 202, if the current number of visible markers 200 on the face 202 is less than five, then the method goes to decision block 290. Otherwise, the method loops to 260.

At decision block 290, the method can determine if there is any alternative face 202 in a visible location, such that another face 202 could potentially have more markers 200 that are visible by the camera 40, as determined from the tracking data 250. If there are no other faces 202 visible, then the method loops to 160. Otherwise, the method goes to decision block 292. At decision block 292, the method can determine if the alternative face 202 is the previous face 202. If the alternative face 202 is the previous face 202, then the method goes to decision block 294. Otherwise, the method goes to 296. At 296, the method can save the current face 202 as the previous face 202. Next, at 298, the method can change the current face 202 to the alternative face 202. The method then loops to 260.

At decision block 294, the method can determine if the number of visible markers 200 on the previous face 202 is greater than or equal to the number of visible markers 200 on the current face 202. If the previous face 202 has a greater number of visible markers 200, then the method can change the current face 202 to the previous face 202 at 300. Then, the method loops to 260. Otherwise, if the previous face 202 has a smaller number of visible markers 200 than the current face 202, then the method keeps the current face 202 and loops to 260.

With reference back to FIG. 4, the face activation control module 238 receives as input the face control data 256 from the face switching control module 236 and the IR sync data 242 from the localizer control module 232. Based on the face control data 256, the face activation control module 238 can activate the desired face 202 of the tracking device 41. The face activation control module 238 can output the IR pulse data 244 comprising the IR pulse 217 to the localizer control module 232 upon the activation of the selected face 202.

Figure 6:
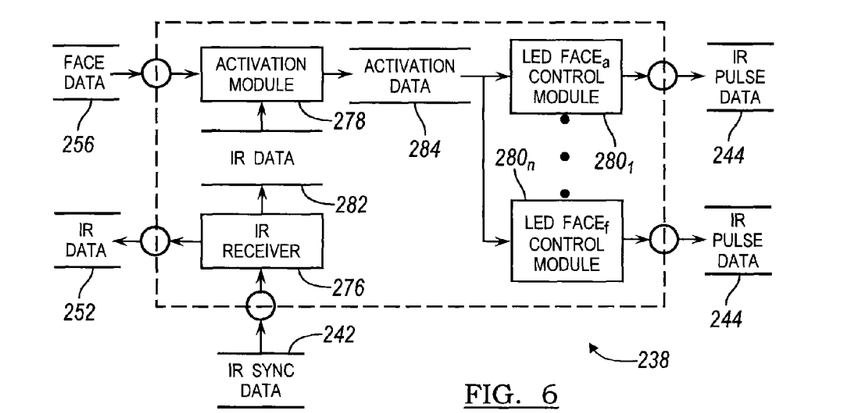
FIG. 6 is a dataflow diagram illustrating an exemplary face activation control system performed by a face activation control module.

For example, with reference to FIG. 6, a dataflow diagram illustrates various embodiments of a face activation system that can be embedded within the face activation control module 238. In various embodiments, the face activation control module 238 can include an IR receiver module 302, an activation module 304, and a plurality of face control modules 306$_a$ to 306$_f$ associated with the respective face 202$_a$ to 202$_f$ of the tracking device 41. It will be understood that although six face control modules 306$_a$ to 306$_f$ are employed with the face activation control module 238, any number of face control modules could be employed.

The IR receiver module 302 can receive as input the IR sync data 242 from the localizer control module 232. On receipt of the IR sync data 242, the IR receiver module 302 sets IR data 252 for the face switching control module 236 to indicate the desired activation of the face 202 of the tracking device 41. The IR receiver module 302 can also set IR data 308 for the activation module 304.

The activation module 304 can receive as input the IR data 308, indicating the receipt of the IR pulse data 244 by the IR receiver module 302, and can also receive as input the face control data 256 from the face switching control module 236. Based on the IR data 308 and face control data 256, the activation module 304 can set activation data 310 for the selected face control modules 306$_a$ to 306$_f$. The activation data 310 can comprise the control signal to activate the selected face 202.

The face control modules 306$_a$ to 306$_f$ can control the activation of each of the selected faces 202 of the tracking device 41, and thus, upon receipt of the activation data 310, the selected face control module 306 can activate the selected face 202. After the selected face 202 has been activated by the face control module 306, the face control module 306 can output the IR pulse data 244.

Thus, during operation, with additional reference to FIGS. 3, 4 and 6, the camera 40 can be initialized to send the initial IR sync 219, from the camera 40 to the receiver 216, and thus, to the IR receiver module 302 of the tracking device 41. Upon receipt of the IR sync 219, the IR receiver module 302 can send IR data 252 to the face switching control module 236 and IR data 308 to the activation module 304. Based on the initial receipt of the IR data 252, the face switching control module 236 can wirelessly transmit face control data 256 to the activation module 304 to activate the face 202. When the activation module 304 receives the face control data 256 and the IR data 308, the activation module 304 can set activation data 310 for the face control module 306 to activate the face 202.

Upon the activation of the face 202, the markers 200 on the face 202 can output the IR pulse 217 for the localizer control module 232. The camera 40, once receiving the IR pulse 217, can send localization data 246 via the localizer control module 232 to the navigation module 234. The navigation module 234 can interpret the localization data 246 and the face control data 256 to determine the position and visibility all of the faces 202. Then, the navigation module 234 can transmit this tracking data 250 to the face switching control module 236. If the face switching control module 236 determines, based on the tracking data 250, that another face 202 of the tracking device 41 is more visible, such that more markers 200 are visible to the camera 40, or better positioned, such that the line-of-sight angle is less than that of the current face 202, the face switching control module 236 can set face control data 256 to instruct the face activation control module 238 to activate the alternative face 202.

Thus, the control module 230 can enable the use of geometrically uniform patterns of markers 200 on each of the faces 202 of the tracking device 41. The use of geometrically uniform patterns of markers 200 enables the formation of smaller tracking devices 41 since each face 202 does not have to have a unique spacing of the markers 200 to be identified by the camera 40. Thus, the control module 230 can allow for the easier navigation of small instruments 42 as the faces 202 of the tracking device 41 can be sized as necessary for the particular instrument while still enabling the identification of the tracking device 41 by the camera 40.

The description of the teachings herein is merely exemplary in nature and, thus, variations that do not depart from the gist of the teachings are intended to be within the scope of the teachings. Such variations are not to be regarded as a departure from the spirit and scope of the teachings.

What is claimed is:

1. A surgical navigation system comprising:
   a tracking device comprising a plurality of planar surfaces, wherein the tracking device includes a receiver that receives a synchronization signal;
   a plurality of sets of pulse emitting markers, wherein each of the plurality of sets of pulse emitting markers is coupled to a respective one of the plurality of planar surfaces, wherein the pulse emitting markers of the plurality of sets of pulse emitting markers generate respective pulse signals, wherein the plurality of sets of pulse emitting markers comprise a first set of pulse emitting markers, wherein the pulse emitting markers in the first set of pulse emitting markers are in a first plane and are coupled to a first planar surface, wherein the first planar surface is in the first plane, and wherein the pulse emitting markers in the first set of pulse emitting markers are configured to emit in a direction perpendicular to the first plane;
   a face activation circuit disposed within the tracking device and configured to generate activation data for the first planar surface of the plurality of planar surfaces based on face control data and the synchronization signal;
   a camera that generates the synchronization signal and receives the pulse signals from the pulse emitting markers coupled to the first planar surface;
   a visibility circuit in communication with the camera, wherein the visibility circuit is configured to
      based on the pulse signals from the pulse emitting markers coupled to the first planar surface, determine a first line-of-sight angle between (i) a vector normal to the first planar surface and (ii) a line-of-sight of the camera, and
      based on the first line-of-sight angle, determine which one of the plurality of planar surfaces is in a better location to be viewed by the camera; and
   a face switching control circuit configured to (i) generate the face control data to activate the set of pulse emitting markers coupled to the one of the plurality of planar surfaces, and (ii) deactivate the other sets of the pulse emitting markers.

2. The surgical navigation system of claim 1, wherein the plurality of sets of pulse emitting markers comprise a light emitting diode or a reflector.

3. The surgical navigation system of claim 1, wherein the plurality of sets of pulse emitting markers form a geometric pattern.

4. The surgical navigation system of claim 3, further comprising an orientating feature to enable the visibility circuit to determine an orientation of the first planar surface.

5. The surgical navigation system of claim 4, wherein the orientating feature comprises at least one offset marker.

6. The surgical navigation system of claim 1, wherein the visibility circuit further comprises:
   a localizer control circuit that (i) receives, from the camera, the pulse signals generated by the pulse emitting markers coupled to the first planar surface, and (ii) transmits localization data based on the pulse signals received from the camera; and
a navigation circuit that generates, based on the localization data, tracking data for the tracking device.

7. The surgical navigation system of claim 6, wherein the tracking data comprises at least one of a location or an orientation of two or more of the plurality of planar surfaces.

8. The surgical navigation system of claim 1, wherein the visibility circuit determines a number of pulse emitting markers coupled to a single one of the plurality of planar surfaces visible to the camera.

9. The surgical navigation system of claim 1, wherein the face switching control circuit wirelessly transmits the face control data to the face activation circuit.

10. The surgical navigation system of claim 1, wherein:
the tracking device is coupled to an instrument; and
the instrument comprises a guide wire, a deep-brain stimulator probe, a catheter, a reference frame microscope, a drill, a drill-guide, a suction device, a biopsy needle, or a cutting guide.

11. The surgical navigation system of claim 1, further comprising an imaging device, wherein the imaging device is one or more of a fluoroscopy device, an O-arm device, a bi-plane fluoroscopy device, an ultrasound device, a computed tomography (CT) device, a multi-slice computed tomography (MSCT) device, a magnetic resonance imaging (MRI) device, a high frequency ultrasound (HFU) device, a positron emission tomography (PET) device, an optical coherence tomography (OCT) device, an intra-vascular ultrasound (IVUS) device, an intra-operative CT device, and an intra-operative MRI device.

12. The surgical navigation system of claim 1, wherein:
the pulse emitting markers which are within view of the camera and coupled to the one of the plurality of planar surfaces have respective line-of-sight angles; and
the line-of-sight angles of the pulse emitting markers which are within view of the camera and coupled to the one of the plurality of planar surfaces which are in view of the camera are each smaller than the line-of-sight angles of the pulse emitting markers coupled to the other ones of the plurality of planar surfaces.

13. The surgical navigation system of claim 1, wherein:
the face activation circuit is configured to generate activation data for a second planar surface of the tracking device;
the camera is configured to receive pulse signals from the set of pulse emitting markers coupled to the second planar surface; and
the visibility circuit is configured to
determine a second line-of-sight angle between (i) a vector normal to the second planar surface and (ii) the line-of-sight of the camera, and
compare the first line-of-sight angle to the second line-of-sight angle, and
based on the comparison between the first line-of-sight angle and the second line-of-sight angle, determine which one of the plurality of planar surfaces is in the better location to be viewed by the camera.

14. The navigation system of claim 1, wherein the plurality of planar surfaces form a geometric shape.

15. The navigation system of claim 1, wherein the geometric shape is a cube.

16. The navigation system of claim 1, wherein each of the sets of pulse emitting markers includes a plurality of pulse emitting markers.

17. The navigation system of claim 1, wherein:
the pulse emitting markers in a second set of the pulse emitting markers are in a second plane; and
the second plane is parallel to or perpendicular to the first plane.

18. The surgical navigation system of claim 15, wherein the face activation circuit, the visibility circuit, the face switching control circuit, the localizer control circuit and the navigation circuit include an application specific integrated circuit, an electronic circuit, a processor, or a combinational logic circuit.

19. A method of tracking a tracking device for use with a surgical navigation system, wherein the tracking device has a plurality of planar surfaces, and wherein each of the plurality of planar surfaces comprises a plurality of markers, the method comprising:
transmitting a synchronization signal from a control circuit or a camera;
activating the markers coupled to a first planar surface of the plurality of planar surfaces such that the markers coupled to the first planar surface emit pulse signals upon receipt of the synchronization signal at the tracking device, wherein the markers coupled to the first planar surface are in a first plane, wherein the first planar surface is in the first plane, and wherein the markers coupled to the first planar surface are configured to emit in a direction perpendicular to the first plane;
tracking the pulse signals emitted by the markers coupled to the first planar surface and in view of the camera;
based on the pulse signals emitted from the markers coupled to the first planar surface, determining a first line-of-sight angle between (i) a vector normal to the first planar surface and (ii) a line-of-sight of the camera; and
based on the first line-of-sight angle determining which one of the plurality of planar surfaces is in a better location to be viewed by the camera;
transmitting an activation signal to the tracking device, wherein the activation signal indicates the one of the plurality of planar surfaces; and
activating the one of the plurality of planar surfaces based on the activation signal.

20. The method of claim 19, wherein the plurality of markers coupled to the first planar surface comprise a light emitting diode or a reflector.

21. The method of claim 19, further comprising:
providing a receiver coupled to the tracking device;
transmitting the synchronization signal to the receiver to charge the markers coupled to the plurality of planar surfaces; and
activating only the markers coupled to the first planar surface upon receipt of the synchronization signal.

22. The method of claim 19, further comprising:
tracking (i) the pulse signals emitted by the markers coupled to the first planar surface, and (ii) pulse signals emitted by the markers coupled to a second planar surface of the tracking device;
determining if the second planar surface is visible to the camera; and
determining if the second planar surface should be activated based on an orientation of the plurality of planar surfaces and the pulse signals from the markers coupled to the first planar surface.

23. The method of claim 19, further comprising:
determining if a first number of markers coupled to the first planar surface which are visible to the camera is greater than or equal to a second number of markers coupled to a second planar surface of the tracking device;

activating the markers coupled to the first planar surface if the first number of markers is greater than or equal to the second number of markers; and activating the markers coupled to the second planar surface if the first number of markers is less than the second number of markers.

24. The method of claim 19, wherein:
generating activation data for a second planar surface of the tracking device;
receiving, at the camera, pulse signals from the markers coupled to the second planar surface;
determining a second line-of-sight angle between (i) a vector normal to the second planar surface and (ii) the line-of-sight of the camera;
comparing the first line-of-sight angle to the second line-of-sight angle; and
based on the comparing of the first line-of-sight angle to the second line-of-sight angle, determining which one of the plurality of planar surfaces is in the better location to be viewed by the camera.

25. The method of claim 19, further comprising:
determining if a first number of markers coupled to the first planar surface which are visible to the camera is less than a total number of markers coupled to the first planar surface;
if the first number of markers coupled to the first planar surface which are visible to the camera is less than the total number of markers coupled to the first planar surface, determining if markers coupled to a second planar surface of the tracking device are visible to the camera; and
if the markers coupled to the second planar surface are visible to the camera,
    determine a second number of markers coupled to the second planar surface which are visible to the camera,
    determine whether the first number of markers is greater than or equal to the second number of markers, and
    if the first number of markers is less than the second number of markers, activate the markers coupled to the second planar surface and deactivate the markers coupled to the first planar surface.

26. A surgical navigation system comprising:
a tracking device having a plurality of planar surfaces, wherein each of the plurality of planar surfaces is illuminated while in an active state;
a plurality of sets of markers, wherein each of the plurality of sets of markers is disposed in each of the plurality of planar surfaces, wherein the markers in the plurality of sets of markers emit respective signals, wherein the plurality of sets of markers comprise a first set of markers, wherein the markers in the first set of markers are in a first plane and are coupled to a first planar surface, wherein the first planar surface is in the first plane, and wherein the markers in the first set of markers are configured to emit in a direction perpendicular to the first plane;
a face activation circuit that activates the markers coupled to the first planar surface of the plurality of planar surfaces upon receipt of an activation signal, wherein a first marker in the first planar surface is activated while a second marker in the first planar surface is activated;
a camera that receives the signals from the markers coupled to the first planar surface; and
a tracking system that
    based on the signals received by the camera, determines a first line-of-sight angle between (i) a vector normal to the first planar surface and (ii) a line-of-sight of the camera, and
    based on the first line-of-sight angle, determines which one of the planar surfaces is in a better location to be viewed by the camera by determining if the first line-of-sight angle for the first planar surface is smaller than a second line-of-sight angle for a second planar surface of the tracking device.

27. The surgical navigation system of claim 26, further comprising an imaging system, wherein the imaging system is one or more of an isocentric fluoroscopy device, an O-arm device, a bi-plane fluoroscopy device, an ultrasound device, a computed tomography (CT) device, a multi-slice computed tomography (MSCT) device, a magnetic resonance imaging (MRI) device, a high frequency ultrasound (HFU) device, a positron emission tomography (PET) device, an optical coherence tomography (OCT) device, an intra-vascular ultrasound (IVUS) device, an intra-operative CT device, and an intra-operative MRI device.

28. The surgical navigation system of claim 26, wherein:
the tracking device includes a receiver; and
the receiver is configured to (i) receive a signal from the camera, and (ii) based on the signal from the camera, charge the markers coupled to one or more of the plurality of planar surfaces of the tracking device.

29. The surgical navigation system of claim 27, wherein the tracking device is adapted to be coupled to the imaging system, an instrument, or an anatomy of a subject.

30. The surgical navigation system of claim 29, wherein the markers coupled to the first planar surface comprise a light emitting diode or a reflector.

31. The surgical navigation system of claim 26, wherein the plurality of planar surfaces provide a three-dimensional cubic structure.

32. The surgical navigation system of claim 26, wherein the plurality of planar surfaces comprises six contiguous planar surfaces.

33. The surgical navigation system of claim 26, wherein the plurality of planar surfaces provide a cubic structure or a hexagonal structure.

34. The surgical navigation system of claim 26, wherein:
the markers in the plurality of planar surfaces comprise sets of markers,
each of the sets of markers (i) is coupled to a respective one of the plurality of planar surfaces, and (ii) includes five light emitting diodes;
one of the light emitting diodes in each of the sets of markers is spaced further away from the other four light emitting diodes in the corresponding set of markers than the four light emitting diodes in the corresponding set of markers are spaced from each other; and
the tracking system determines an orientation of the tracking device based on one or more light patterns provided due to differences in distances between the light emitting diodes on each of the plurality of planar surfaces.

35. The surgical navigation system of claim 26, wherein:
the face activation circuit is configured to generate activation data for the second planar surface of the tracking device;
the camera is configured to receive signals from the markers coupled to the second planar surface; and
the tracking system is configured to determine the second line-of-sight angle between (i) a vector normal to the second planar surface and (ii) the line-of-sight of the camera.

* * * * *